United States Patent
Pu et al.

(10) Patent No.: US 8,551,010 B2
(45) Date of Patent: Oct. 8, 2013

(54) RESPIRATION MONITORING FOR HEART FAILURE USING IMPLANTABLE DEVICE

(75) Inventors: Yachuan Pu, Laguna Niguel, CA (US); Kent Lee, Shoreview, MN (US); Jonathan Kwok, Holmdel, NJ (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/553,098

(22) Filed: Jul. 19, 2012

(65) Prior Publication Data
US 2012/0283527 A1 Nov. 8, 2012

Related U.S. Application Data

(63) Continuation of application No. 11/463,076, filed on Aug. 8, 2006, now Pat. No. 8,226,570.

(51) Int. Cl.
*A61B 5/08* (2006.01)

(52) U.S. Cl.
USPC ............................ 600/534; 600/484; 600/529

(58) Field of Classification Search
USPC .................................................. 600/429–543
See application file for complete search history.

(56) References Cited

U.S. PATENT DOCUMENTS

| | | | |
|---|---|---|---|
| 5,303,702 A | 4/1994 | Bonnet et al. | |
| 6,045,513 A | 4/2000 | Stone et al. | |
| 6,076,015 A | 6/2000 | Hartley et al. | |
| 6,454,719 B1 | 9/2002 | Greenhut | |
| 6,512,949 B1 | 1/2003 | Combs et al. | |
| 6,589,188 B1 | 7/2003 | Street et al. | |
| 6,600,949 B1 | 7/2003 | Turcott | |
| 6,830,548 B2 | 12/2004 | Bonnet et al. | |
| 6,856,829 B2 | 2/2005 | Ohsaki et al. | |
| 6,904,320 B2 | 6/2005 | Park et al. | |

(Continued)

FOREIGN PATENT DOCUMENTS

| EP | 1151718 A2 | 11/2001 |
|---|---|---|
| EP | 1151718 A3 | 9/2002 |

(Continued)

OTHER PUBLICATIONS

U.S. Appl. No. 11/900,049, filed Sep. 7, 2007, Periodic Breathing During Activity.

(Continued)

*Primary Examiner* — Michael Kahelin
*Assistant Examiner* — Karen Toth
(74) *Attorney, Agent, or Firm* — Schwegman Lundberg & Woessner, P.A.

(57) ABSTRACT

An implantable respiration monitor can be used to detect disordered breathing or periodic breathing events that can be categorized, such as according to one or more of sleep, exercise, and resting awake states. The categorized frequency of such events can be compared to independently specifiable thresholds, such as to trigger an alert or responsive therapy, or to display one or more trends. The information can also be combined with detection of one or more other congestive heart failure (CHF) symptoms to generate a CHF status indicator or to trigger an alarm or responsive therapy or to display one or more trends. The alert can notify the patient or a caregiver, such as via remote monitoring. The sleep state information can be further categorized according to central sleep apnea (CSA) or obstructive sleep apnea (OSA) events.

20 Claims, 5 Drawing Sheets

(56) References Cited

U.S. PATENT DOCUMENTS

| | | | |
|---|---|---|---|
| 7,025,730 | B2 | 4/2006 | Cho et al. |
| 7,094,207 | B1 | 8/2006 | Koh |
| 7,103,410 | B2 | 9/2006 | Kramer et al. |
| 7,160,252 | B2 | 1/2007 | Cho et al. |
| 7,245,970 | B2 | 7/2007 | Zhu et al. |
| 7,329,226 | B1 | 2/2008 | Ni et al. |
| 7,697,990 | B2 * | 4/2010 | Ujhazy et al. ............ 607/42 |
| 7,704,211 | B1 | 4/2010 | Koh |
| 8,226,570 | B2 | 7/2012 | Pu et al. |
| 2005/0074741 | A1 | 4/2005 | Lee et al. |
| 2005/0085868 | A1 | 4/2005 | Tehrani et al. |
| 2005/0113710 | A1 | 5/2005 | Stahmann et al. |
| 2005/0148897 | A1 | 7/2005 | Cho et al. |
| 2005/0165457 | A1 | 7/2005 | Benser et al. |
| 2006/0217603 | A1 | 9/2006 | Nagai et al. |
| 2006/0293604 | A1 | 12/2006 | Carlson et al. |
| 2007/0073169 | A1 | 3/2007 | Averina et al. |
| 2007/0073171 | A1 | 3/2007 | Cho et al. |
| 2007/0073181 | A1 | 3/2007 | Pu et al. |
| 2007/0129643 | A1 * | 6/2007 | Kwok et al. ............ 600/529 |
| 2007/0167843 | A1 * | 7/2007 | Cho et al. ............ 600/484 |
| 2007/0239057 | A1 | 10/2007 | Pu et al. |
| 2008/0039730 | A1 | 2/2008 | Pu et al. |
| 2008/0071185 | A1 | 3/2008 | Beck et al. |

FOREIGN PATENT DOCUMENTS

| | | |
|---|---|---|
| WO | WO-9834537 | 8/1998 |
| WO | WO-2005037077 A2 | 4/2005 |
| WO | WO-2007038705 A2 | 4/2007 |

OTHER PUBLICATIONS

U.S. Appl. No. 11/463,076, filed Aug. 8, 2006, Respiration Monitoring for Heart Failure Using Implantable Device.

U.S. Appl. No. 11/514,423, filed Sep. 1, 2006, Respiration Monitoring Using Respiration Rate Variability.

U.S. Appl. No. 11/392,365, filed Mar. 29, 2006, Periodic Disordered Breathing Detection.

"U.S. Appl. No. 11/900,049, Final Office Action mailed Dec. 7, 2011", 12 pgs.

"U.S. Appl. No. 11/900,049, Pre-Appeal Brief Request filed Mar. 30, 2012", 5 pgs.

Pu, Yachuan, et al., "Periodic Disordered Breathing Detection", U.S. Appl. No. 11/392,365, filed Mar. 29, 2006, 34 pgs.

"U.S. Appl. No. 11/463,076, Examiner Interview Summary mailed Oct. 19, 2011", 3 pgs.

"U.S. Appl. No. 11/463,076, Final Office Action mailed Jul. 11, 2011", 11 pgs.

"U.S. Appl. No. 11/463,076, Non Final Office Action mailed Nov. 26, 2010", 13 pgs.

"U.S. Appl. No. 11/463,076, Notice of Allowance mailed Apr. 3, 2012", 8 pgs.

"U.S. Appl. No. 11/463,076, Response filed Apr. 26, 2011 to Non-Final Office Action mailed Nov. 26, 2010", 12 pgs.

"U.S. Appl. No. 11/463,076, Response filed Sep. 7, 2010 to Restriction Requirement mailed Aug. 5, 2010", 9 pgs.

"U.S. Appl. No. 11/463,076, Response filed Oct. 11, 2011 to Final Office Action mailed Jul. 11, 2011", 12 pgs.

"U.S. Appl. No. 11/463,076, Restriction Requirement mailed Aug. 5, 2010", 7 pgs.

"U.S. Appl. No. 11/900,049, Non Final Office Action mailed Jun. 9, 2011", 11 pgs.

"U.S. Appl. No. 11/900,049, Response filed Sep. 9, 2011 to Non-Final Office Action mailed Jun. 9, 2011", 13 pgs.

Corra, U., et al., "Oscillatory ventilation during exercise in patients with chronic heart failure: clinical correlates and prognostic implications", Chest, 121(5), (May 2002), 1572-80.

Corra, U., et al., "Sleep and exertional periodic breathing in chronic heart failure: prognostic importance and interdependence", Circulation, 113(1), (Jan. 3, 2006), 44-50.

Francis, D. P., et al., "Quantitative general theory for periodic breathing in chronic heart failure and its clinical implications.", Circulation, 102(18), (Oct. 31, 2000), 2214-21.

Khoo, Michael, et al., "Determinants of ventilatory instability and variability.", Respir Physiol., 122(2-3), (Sep. 2000), 167-82.

Leite, J. J., et al., "Periodic breathing during incremental exercise predicts mortality in patients with chronic heart failure evaluated for cardiac transplantation", J Am Coll Cardiol., 41(12), (Jun. 18, 2003), 2175-81.

Olson, T. P., et al., "Exercise-disordered breathing in chronic heart failure.", Exerc Sport Sci Rev., 34(4), (Oct. 2006), 194-201.

Ribeiro, J. P., "Periodic breathing in heart failure: bridging the gap between the sleep laboratory and the exercise laboratory", Circulation, 113(1), (Jan. 3, 2006), 9-10.

* cited by examiner

RESPIRATION MONITORING FOR HEART FAILURE USING IMPLANTABLE DEVICE

CLAIM OF PRIORITY

This application is a continuation of and claims the benefit of priority under 35 U.S.C. §120 to Pu et al., U.S. patent application Ser. No. 11/463,076, entitled "RESPIRATION MONITORING FOR HEART FAILURE USING IMPLANTABLE DEVICE," filed on Aug. 8, 2006, which is hereby incorporated by reference herein in its entirety.

TECHNICAL FIELD

This patent document pertains generally to disordered breathing and congestive heart failure and more particularly, but not by way of limitation, to categorizing, such as by using sleep and exercise states, respiration monitored using implantable device, such as for heart failure status monitoring.

BACKGROUND

Sleep is generally beneficial and restorative to a person. Therefore, it exerts a great influence on a person's quality of life. The human sleep/wake cycle generally conforms to a circadian rhythm that is regulated by a biological clock. Regular periods of sleep enable the body and mind to rejuvenate and rebuild. The body may perform various tasks during sleep, such as organizing long term memory, integrating new information, and renewing tissue and other body structures.

Lack of sleep and/or decreased sleep quality may have a number of causal factors including, e.g., respiratory disturbances, nerve or muscle disorders, and emotional conditions, such as depression and anxiety. Chronic long-term sleep-related disorders such as chronic insomnia, sleep-disordered breathing, and sleep movement disorders may significantly affect a patient's sleep quality and quality of life.

Sleep apnea, for example, is a fairly common breathing disorder characterized by periods of interrupted breathing experienced during sleep. Sleep apnea is typically classified based on its etiology. One type of sleep apnea, denoted as obstructive sleep apnea, occurs when the patient's airway is obstructed by the collapse of soft tissue in the rear of the throat. Central sleep apnea is caused by a derangement of the central nervous system control of respiration. The patient ceases to breathe when control signals from the brain to the respiratory muscles are absent or interrupted. Mixed apnea is a combination of the central and obstructive sleep apnea types. Regardless of the type of apnea people experiencing an apnea event stop breathing for a period of time. The cessation of breathing may occur repeatedly during sleep, sometimes hundreds of times a night and occasionally for a minute or longer.

In addition to apnea, other types of disordered breathing have been identified, including, for example, hypopnea (shallow breathing), dyspnea (labored breathing), hyperpnea (deep breathing), and tachypnea (rapid breathing). Combinations of the disordered respiratory events described above have also been observed. For example, Cheyne-Stokes respiration (CSR, which is sometimes referred to as periodic breathing) is associated with rhythmic increases and decreases in tidal volume caused by alternating periods of hyperpnea followed by apnea or hypopnea. The breathing interruptions of CSR may be associated with central apnea, or may be obstructive in nature. CSR is frequently observed in patients with congestive heart failure (CHF) and is associated with an increased risk of accelerated CHF progression.

OVERVIEW

An implantable respiration monitor can be used to detect disordered breathing or periodic breathing events that can be categorized, such as according to one or more of sleep, exercise, and resting awake states. The categorized frequency of such events can be compared to independently specifiable thresholds, such as to trigger an alert or responsive therapy, or to display one or more trends. The information can also be combined with detection of one or more other congestive heart failure (CHF) symptoms to generate a CHF status indicator or to trigger an alarm or responsive therapy or to display one or more trends. The alert can notify the patient or a caregiver, such as via remote monitoring. The sleep state information can be further categorized according to central sleep apnea (CSA) or obstructive sleep apnea (OSA) events.

In Example 1, a system includes a sleep detector, adapted to detect a sleep indication in a subject, the sleep indication providing an indication or inference of whether the subject is asleep or awake. The system also includes an exercise detector, adapted to detect an exercise indication in the subject, the exercise indication providing an indication or inference of whether the subject is active or at rest. The system also includes an implantable respiration monitor, operatively coupled to the sleep and exercise detectors, the respiration monitor adapted to detect disordered breathing in the subject, and to compute at least two of: a sleep disordered breathing indication, an exercise disordered breathing indication, and a resting awake disordered breathing indication.

In Example 2, the system of Example 1 optionally includes an alert module, operatively coupled to the respiration monitor, the alert module generating an alert in response to an abnormal value of at least one of: the sleep disordered breathing indication, the exercise disordered breathing indication, and the resting awake disordered breathing indication.

In Example 3, the system of Examples 1-2 optionally includes an ambulatory therapy module, operatively coupled to the alert module, the ambulatory therapy module configured to automatically initiate or adjust therapy in response to the alert.

In Example 4, the system of Examples 1-3 optionally includes an alert module, operatively coupled to the respiration monitor, the alert module generating an alert in response to at least a specified increase in at least one of the sleep disordered breathing indication, the exercise disordered breathing indication, and the resting awake disordered breathing indication.

In Example 5, the system of Examples 1-4 optionally includes an ambulatory therapy module, operatively coupled to the alert module, the ambulatory therapy module configured to automatically initiate or adjust therapy in response to the alert.

In Example 6, the system of Examples 1-5 optionally includes an alert module, operatively coupled to the respiration monitor, the alert module generating an alert in response to at least an abnormal value or a specified increase in at least two of: the sleep disordered breathing indication, the exercise disordered breathing indication, and the resting awake disordered breathing indication.

In Example 7, the system of Examples 1-6 optionally includes an ambulatory therapy module, operatively coupled to the alert module, the ambulatory therapy module configured to automatically initiate or adjust therapy in response to the alert.

In Example 8, the system of Examples 1-7 optionally include an auxiliary congestive heart failure (CHF) indication detector, and an alert module, operatively coupled to the respiration monitor and the auxiliary CHF indication detector, the alert module generating an alert in response to an indication of CHF received from the CHF indication detector and an abnormal value or a specified increase of at least one of: the sleep disordered breathing indication, the exercise disordered breathing indication, and the resting awake disordered breathing indication.

In Example 9, the system of Examples 1-8 are optionally configured such that the auxiliary CHF indication detector includes a pulmonary fluid status indicator, and in which the indication of CHF received from the CHF indication detector includes an indication of an abnormally high level of pulmonary fluid.

In Example 10, the system of Examples 1-9 are optionally configured such that the auxiliary CHF indication detector includes at least one of a pulmonary artery pressure sensor, a heart sound sensor, a heart rate variability detector, a patient weight indicator, and a patient activity detector.

In Example 11, the system of Examples 1-10 optionally include an ambulatory therapy module, operatively coupled to the alert module, the ambulatory therapy module configured to automatically initiate or adjust therapy in response to the alert.

In Example 12, the system of Examples 1-11 is optionally configured such that the respiration monitor comprises a respiration detector circuit, adapted to detect a respiration signal from the subject, an envelope detector circuit, adapted to detect an envelope of the respiration signal, and an envelope variation detector circuit, adapted to detect a variation in the envelope representing disordered breathing.

In Example 13, the system of Examples 1-12 is optionally configured such that the respiration monitor comprises means for detecting a respiration signal from the subject, and means for detecting separate indications of periodic breathing in each of sleep, exercise, and resting awake states.

In Example 14, the system of Examples 1-13 optionally includes an external display configured to display information about at least one of a sleep disordered breathing indication, an exercise disordered breathing indication, and a resting awake disordered breathing indication.

In Example 15, the system of Examples 1-14 optionally is configured such that it includes a display that is configured to display a trend over time of at least one of a sleep disordered breathing indication, an exercise disordered breathing indication, and a resting awake disordered breathing indication.

In Example 16, the system of Examples 1-15 optionally includes an apnea classifier, configured to distinguish between obstructive sleep apnea (OSA) and central sleep apnea (CSA), and the sleep disordered breathing indication uses information from the apnea classifier to determine the sleep disordered breathing indication.

In Example 17, a method includes monitoring respiration of a subject, detecting sleep of the subject, detecting exercise of the subject, and determining at least two of a sleep disordered breathing indication, an exercise disordered breathing indication and a resting awake disordered breathing indication.

In Example 18, the method of Example 17 optionally includes generating an alert in response to an abnormal value of at least one of: the sleep disordered breathing indication, the exercise disordered breathing indication, and the resting awake disordered breathing indication.

In Example 19, the method of Examples 17-18 optionally includes automatically delivering a therapy in response to the alert.

In Example 20, the method of Examples 17-19 optionally includes monitoring an auxiliary indication of congestive heart failure of the subject, and generating an alert in response to an abnormal value of the auxiliary indication of congestive heart failure and an abnormal value of at least one of: the sleep disordered breathing indication, the exercise disordered breathing indication, and the resting awake disordered breathing indication.

In Example 21, the method of Examples 17-20 is optionally configured such that the monitoring an auxiliary indication of congestive heart failure includes monitoring at least one of a pulmonary fluid accumulation, a pulmonary artery pressure, a heart sound, a heart rate variability, a patient weight, and a patient activity level.

In Example 22, the method of Examples 17-21 optionally includes automatically delivering a therapy in response to the alert.

In Example 23, the method of Examples 17-22 optionally includes determining a sleep disordered breathing indication, an exercise disordered breathing indication and a resting awake disordered breathing indication.

In Example 24, the method of Examples 17-23 optionally includes generating an alert in response to an abnormal value or a specified increase of at least two of the sleep disordered breathing indication, the exercise disordered breathing indication, and the resting awake disordered breathing indication.

In Example 25, the method of Examples 17-24 optionally includes automatically delivering a therapy in response to the alert.

In Example 26, the method of Examples 17-25 optionally includes displaying information about at least one of a sleep disordered breathing indication, an exercise disordered breathing indication, and a resting awake disordered breathing indication.

In Example 27, the method of Examples 17-26 optionally includes detecting one or more apnea events, classifying the one or more apnea events as obstructive sleep apnea (OSA) or central sleep apnea (CSA), and determining the sleep disordered breathing indication using information about the classification of the one or more apnea events as OSA or CSA.

In Example 28, the method of Examples 17-27 optionally includes determining a first sleep disordered breathing indication using only CSA events.

In Example 29, the method of Examples 17-27 optionally includes determining a second sleep disordered breathing indication using only OSA events.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
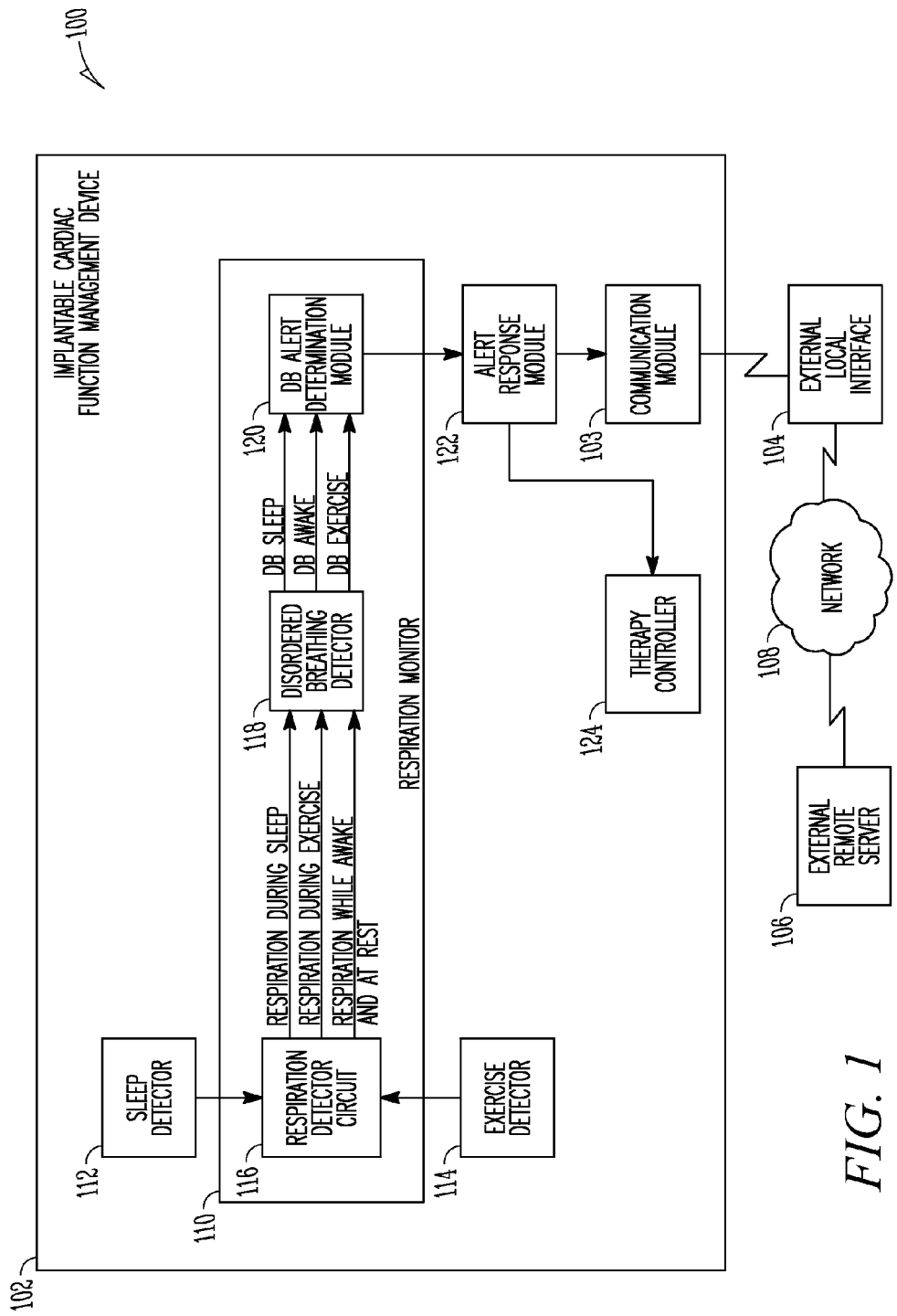
FIG. 1 is a block diagram illustrating generally an example of a system including an implantable device, which is typically wirelessly communicatively coupled by a communication module to an external local interface, which, in turn is communicatively coupled to an external remote server, such as over a wired or wireless telecommunications or computer network.

FIG. 1 is a block diagram illustrating generally an example of a system 100 including an implantable device 102, which is typically wirelessly communicatively coupled by a communication module 103 to an external local interface 104, which, in turn is communicatively coupled to an external remote server 106, such as over a wired or wireless telecommunications or computer network 108. In certain examples, the implantable device 102 includes an implantable cardiac function management device 102, such as a pacer, cardioverter, defibrillation, cardiac resynchronization therapy (CRT) device, or a combination device that combines these or other functions, such as patient monitoring, therapy control, or the like.

In this example, the implantable device 102 can include a hermetically sealed housing to carry electronics, and can include a respiration monitor 110, a sleep detector circuit 112, and an exercise detector circuit 114. In the example of FIG. 1, the respiration monitor 110 includes a respiration detector circuit 116 that transduces a subject's breathing into an electrical signal representative of such breathing. An example of a respiration detector circuit 116 is a transthoracic impedance sensor, which detects variations in transthoracic impedance as a subject inhales and exhales, such as described in Hartley et al. U.S. Pat. No. 6,076,015, which is incorporated herein by reference in its entirety, including its description of an impedance-based respiration detector. In other examples, a respiration signal can be derived from detected heart sounds, detected blood pressures, or one or more other proxy parameters. An example of a sleep detector 112 is described in Yousafali Dalal et al. U.S. patent application Ser. No. 11/458,602, entitled "SLEEP STATE DETECTION", filed on Jul. 19, 2006, which is incorporated by reference in its entirety, including its description of a sleep detector. An example of an exercise detector 114, is an accelerometer, which can be configured to produce a signal representative of the subject's activity, which, in turn, can be signal-processed to obtain an indication of a representative level of activity. For example, a rate-responsive pacer may already include an accelerometer-based exercise detector to determine a patient activity level, so that the pacing rate can be adjusted according to the patient activity level to adjust cardiac output according to a perceived metabolic need for such cardiac output.

In the example shown in FIG. 1, the respiration detector circuit 116 can receive a sleep or awake indication from the sleep detector 112, and an exercise or resting indication from the exercise detector 114. The respiration detector circuit 116 can output responsive signals indicative of respiration during sleep, respiration during exercise, and respiration while awake and at rest. In the example of FIG. 1, such signals are received by a disordered breathing detector 118. Although FIG. 1 has been illustrated, for conceptual clarity, as having separate signals representing respiration during sleep, respiration during exercise, and respiration while awake and at rest, it is understood that the disordered breathing detector 118 can alternatively be implemented to receive a single respiration signal, together with sleep/awake information from the sleep detector 112 and exercise/rest information from the exercise detector 114.

However implemented, the disordered breathing detector 118 will typically compute a separate indication of the amount of disordered breathing occurring during at least one of sleep, exercise, and resting awake states, which can be denoted as $DB_{sleep}$, $DB_{exercise}$, and $DB_{rest}$, respectively. More typically, the disordered breathing detector 118 will typically compute separate indications of the amount of disordered breathing occurring during at least two of sleep, exercise, and resting awake states, which can be denoted as $DB_{sleep}$, $DB_{exercise}$, and $DB_{rest}$, respectively. Even more typically, the disordered breathing detector 118 will compute three separate indications of the amount of disordered breathing occurring during each of sleep, exercise, and resting awake states.

Such disordered breathing can include incidences of apnea. Apnea occurs when breathing stops for a brief period, which may then be followed by hyperventilation. In certain examples, cessation of breathing for a period of at least 10 seconds is deemed an apnea event. Sleep disordered breathing can also include incidences of hypopnea. Hypopnea occurs when breathing amplitude decreases for a brief period, which may then also be followed by hyperventilation. In certain examples, a drop in breathing amplitude by at least 30%-50% (and which does not constitute apnea) for a period of at least 10 seconds is deemed a hypopnea event. An apnea-hypopnea index (AHI) can be defined as the number of apnea and hypopnea events during a period of sleep divided by the duration of that period of sleep.

However, disordered breathing can also include hypopnea events that can occur even if the patient is awake, such as when the patient is awake and resting, or when the patient is awake and exercising. Whether when awake or asleep, if such hypopnea events become frequent enough, they can be deemed periodic breathing, which can be conceptualized as a recurring cycle of a hypopnea event, which followed by a period of respiration (which is often hyperventilation to offset the hypopnea). Hypopnea events or periodic breathing occurring during exercise, for example, is believed to have different clinical significance than such incidences occurring during sleep, and such incidences occurring when the subject is awake but at rest. Periodic breathing during exercise is sometimes referred to as exertional oscillatory ventilation (EOV). In general, patients having AHI<30 and no EOV are believed to expect a better survival rate than patients with EOV alone, who are believed, in turn, to expect a better survival rate than patients with AHI>30 alone (but no EOV), who are believed, in turn, to expect a better survival rate than patients with combined breathing disorder (CBD), that is, both AHI>30 and EOV. Thus, by categorizing disordered breathing, such as according to sleep, exercise, and resting awake states, a more accurate patient wellness indicator can be created than by computing disordered breathing without distinguishing between whether such disordered breathing occurs during a sleep, an exercise, or a resting awake state. Such more specific wellness indicator(s) can be provided to an alert determination module 120 and used to provide a more accurate alert, such as to the patient, to the patient's physician, or to the patient's personal medical device that initiates or adjusts one or more responsive therapies. In the example of FIG. 1, the alert determination module 120 can provide resulting alert to an alert response module 122, which can sound a buzzer, or communicate an alert via communication module 103 to external local interface 104 (e.g., a patient interface), or to an external remote server 106, which can provide remote monitoring and notification of the patient or the patient's physician. Alternatively or additionally, in the example of FIG. 1, the alert response module 122 can provide closed-loop feedback to a therapy controller 124, which can initiate or adjust one or more congestive heart failure (CHF) or other therapies to be automatically delivered to the patient, such as cardiac resynchronization therapy (CRT), drug delivery, or any other suitable responsive therapy. Examples of CRT include, without limitation, adjusting AV delay, adjusting interventricular pacing delay, adjusting intraventricular pacing delay, adjusting intraventricular electrode selection, adjusting cardiac contractility modulation (CCM) therapy, or the like.

The disordered breathing detector 118 can be configured to count a number of apnea or hypopnea events, and to compute an overall unweighted disordered breathing severity indication. In certain examples, this disordered breathing severity indication can be determined using a "density" (e.g., frequency or rate of occurrence) of such events per unit time. Similarly, the disordered breathing detector 118 can be configured to compute separate disordered breathing severity indications for sleep, exercise, and awake and resting states. Such separate disordered breathing severity indications for sleep, exercise, and awake and resting states can be separately (e.g., differently) weighted and combined into an overall weighted disordered breathing severity indication, which can in certain examples represent a density of such events per unit time. The disordered breathing severity indication can additionally or alternatively use other information to determine severity, such as a duration of a disordered breathing episode, a measure of the amount of decrease of the respiration amplitude during the episode, or any other information that is indicative of the severity of the disordered breathing episode.

Figure 2:
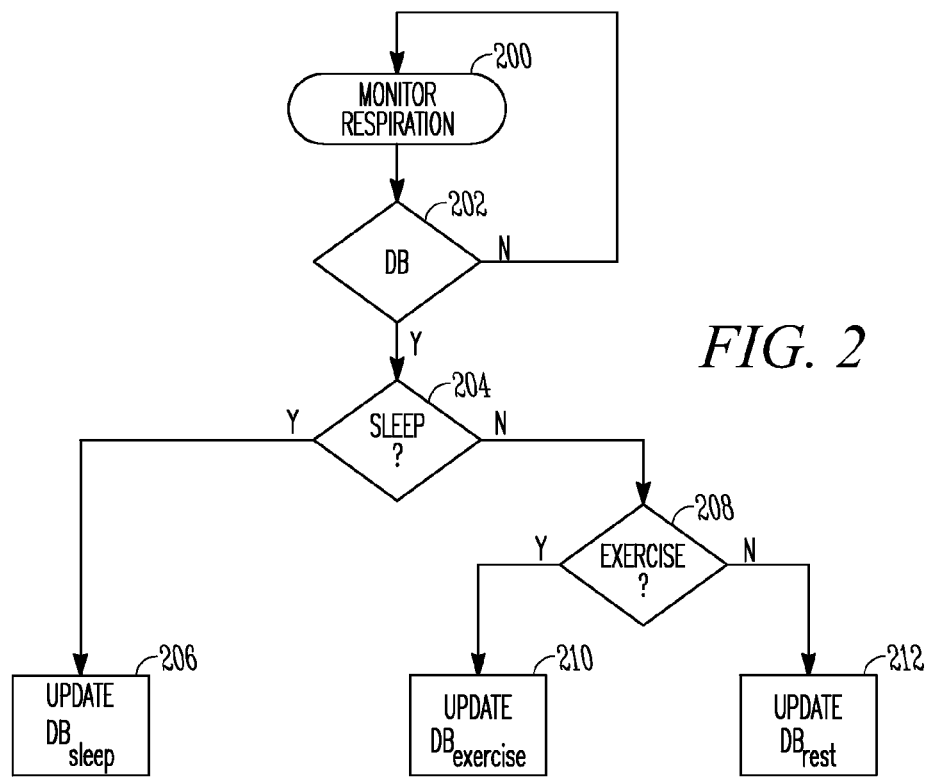
FIG. 2 is a flow chart illustrating generally an example of portions of a technique for monitoring disordered breathing.

FIG. 2 is a flow chart illustrating generally an example of portions of a technique for monitoring disordered breathing. In the example of FIG. 2, at 200, respiration is monitored for incidences of disordered breathing, such as an apnea event or a hypopnea event, as discussed above. At 202, if such a disordered breathing (DB) event is detected, then at 204, it is determined whether the subject was sleeping, otherwise process flow returns to 200. At 204, if the subject was sleeping when the DB event was detected, then a DBsleep density or severity indicator is updated at 206. In certain examples, this can involve computing an inverse of a time period since the last DB event was detected in either a sleep, exercise, or resting state, and including this value in a buffer of the N most recent similar values occurring during sleep. At 204, if the subject was not sleeping when the DB event was detected, then at 208 it is determined whether the subject was exercising when the DB event was detected. If so, then at 210, a DBexercise density or severity indicator is updated, similar to the updating of the DBsleep density or severity indicator at 206. Otherwise, then at 212, a DBrest density or severity indicator is updated, similar to the updating of the DBexercise density or severity indicator at 210 and the DBsleep density or severity indicator at 206. In this manner, separate indications of the severity or density over time of disordered breathing are computed for the sleep, exercise, and awake but resting states.

Figure 3:
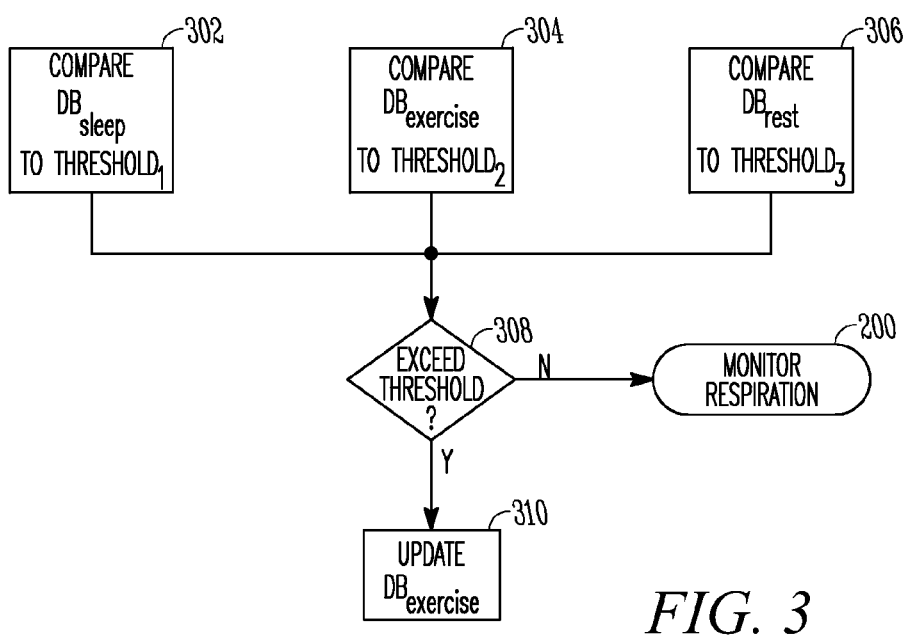
FIG. 3 is a flow chart illustrating generally an example of how the indicators of disordered breathing density or frequency during sleep, exercise, and rest can be used.

FIG. 3 is a flow chart illustrating generally an example of how the DBsleep density or severity indicator, the DBexercise density or severity indicator, and the DBrest density or severity indicator can be used. At 302, the DBsleep density or severity indicator is compared to a threshold value, which can be programmed specifically for the DBsleep density or severity indicator. At 304, the DBexercise density or severity indicator is compared to a threshold value, which can be programmed specifically for the DBexercise density or severity indicator. At 306, the DBrest density or severity indicator is compared to a threshold value, which can be programmed specifically for the DBrest density or severity indicator. At 308, if at least two of these comparisons exceed their respective threshold value, then an alert is triggered at 310, otherwise process flow returns to 200, where respiration monitoring continues.

Variations on this technique are also possible. For example, at 308, the condition could be defined such that if at least one of the comparisons exceeds its respective threshold value, then an alert is triggered at 310. Alternatively, at 308, the condition could be defined such that all three comparisons must exceed their respective threshold values for the alert to be triggered at 310. In any of these various examples, the corresponding threshold can optionally be set using a long-term average or baseline of the particular one of the DBsleep density or severity indicator, the DBexercise density or severity indicator, and the DBrest density or severity indicator. In this manner, an alert will only be triggered if there is a more than insubstantial (e.g., 3 standard deviations above baseline) change in one or more than one of such density or severity indicators, depending on which test condition is used.

Figure 4:
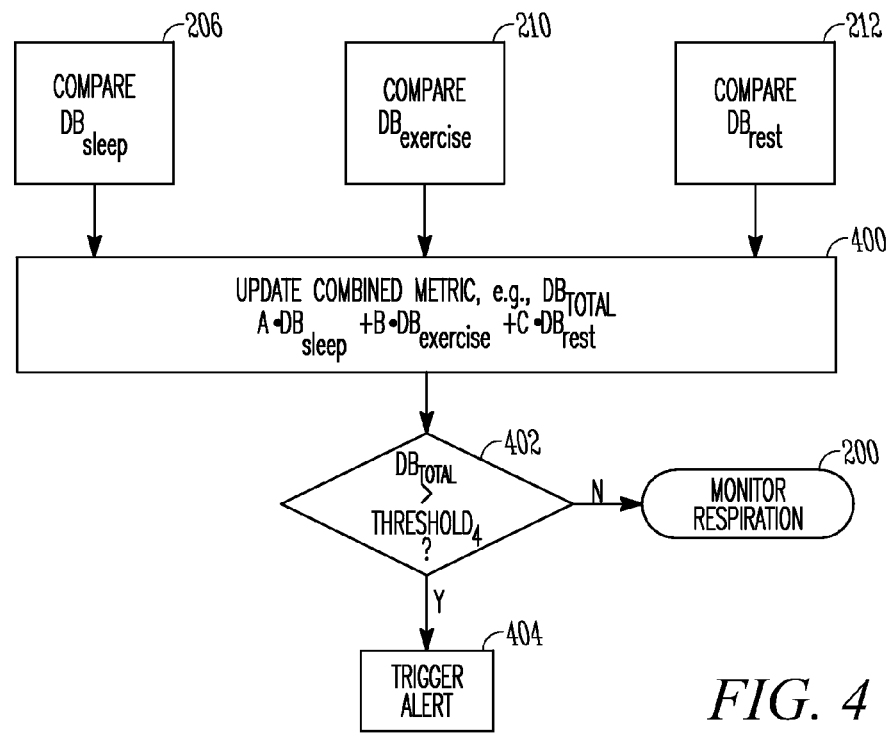
FIG. 4 is a flow chart illustrating generally an example of how such indicators can be used to form a combined metric.

FIG. 4 is a flow chart illustrating generally an example of how the updated DBsleep indicator, the DBexercise indicator, and the DBrest indicator can be used. After these respective indicators are updated, such as at 206, 210, and 212, respectively, then at 400, a combined metric DBtotal is updated, such as according to DBtotal=A·DBsleep+B·DBexercise+C·DBrest, where A, B, C are independently specified scaling values. Then, at 402, the combined metric DBtotal is compared to a corresponding threshold value. If, at 402, DBtotal exceeds its corresponding threshold value, then at 404 an alert is triggered, otherwise process flow returns to the respiration monitoring at 200.

In certain variations of the above technique, the combined metric DBtotal is logged, such as on a daily basis. Moreover, the threshold to which the DBtotal metric is compared can be set based on a baseline long-term value of the same metric, or based on the baseline value and variance (e.g., threshold at +3 standard deviations above baseline).

Figure 5:
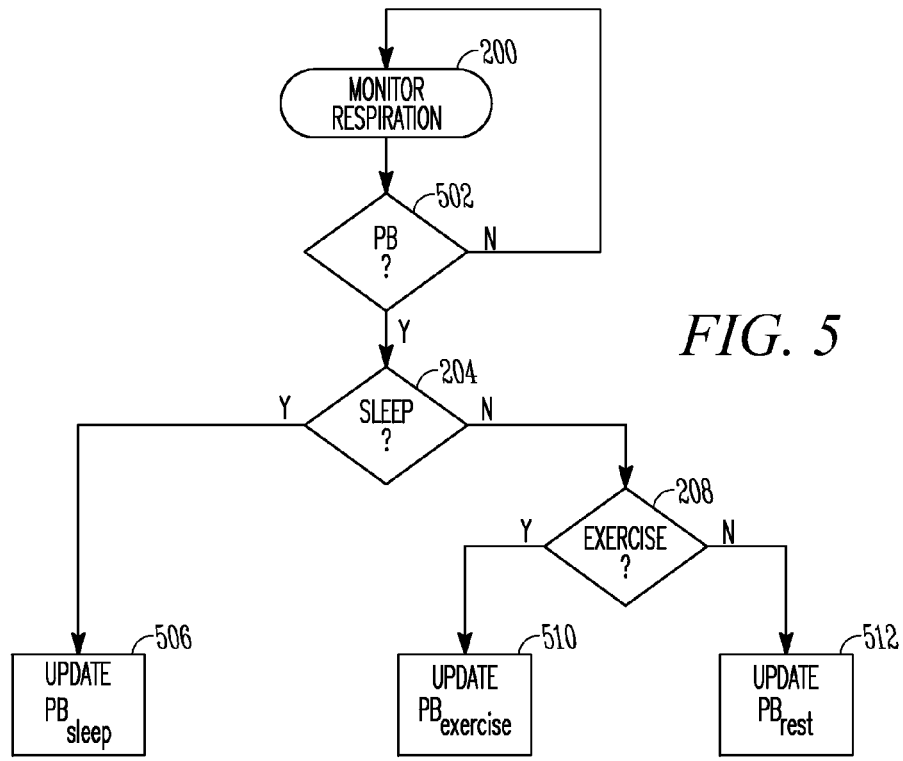
FIG. 5 is a flow chart, similar to FIG. 2, but illustrating a technique in which a periodic breathing (PB) event is detected, instead of the detecting of a disordered breathing (DB) event in FIG. 2.

FIG. 5 is a flow chart, similar to FIG. 2, but illustrating a technique in which a periodic breathing (PB) event is detected at 502, instead of detecting a disordered breathing (DB) event at 202 of FIG. 2. A PB event can be conceptualized as a DB event (e.g., apnea or hypopnea) that is recurring often enough and with sufficient periodicity to be considered periodic breathing instead of a series of isolated DB events. One example of disordered breathing is described in Yachuan Pu et al. U.S. patent application Ser. No. 11/392,365 entitled "PERIODIC DISORDERED BREATHING DETECTION", filed on Mar. 28, 2006, which is incorporated herein by reference in its entirety, including its description of detecting periodic breathing. In brief, periodic breathing can be detected by rectifying the respiration signal, and lowpass filtering the rectified signal (e.g., such as with a moving average) to obtain an "envelope" signal. The resulting envelope signal can be further filtered (e.g., highpass filtered to remove baseline wander) and then tested for amplitude variations of sufficient magnitude to constitute periodic breathing. Periodic breathing density or severity indicators can be computed for sleep, exercise, or resting states at 506, 510, and 512 respectively, similarly to the above description of computing disordered breathing density or severity indicators for similar states at 206, 210, and 212, respectively of FIG. 2.

Figure 6:
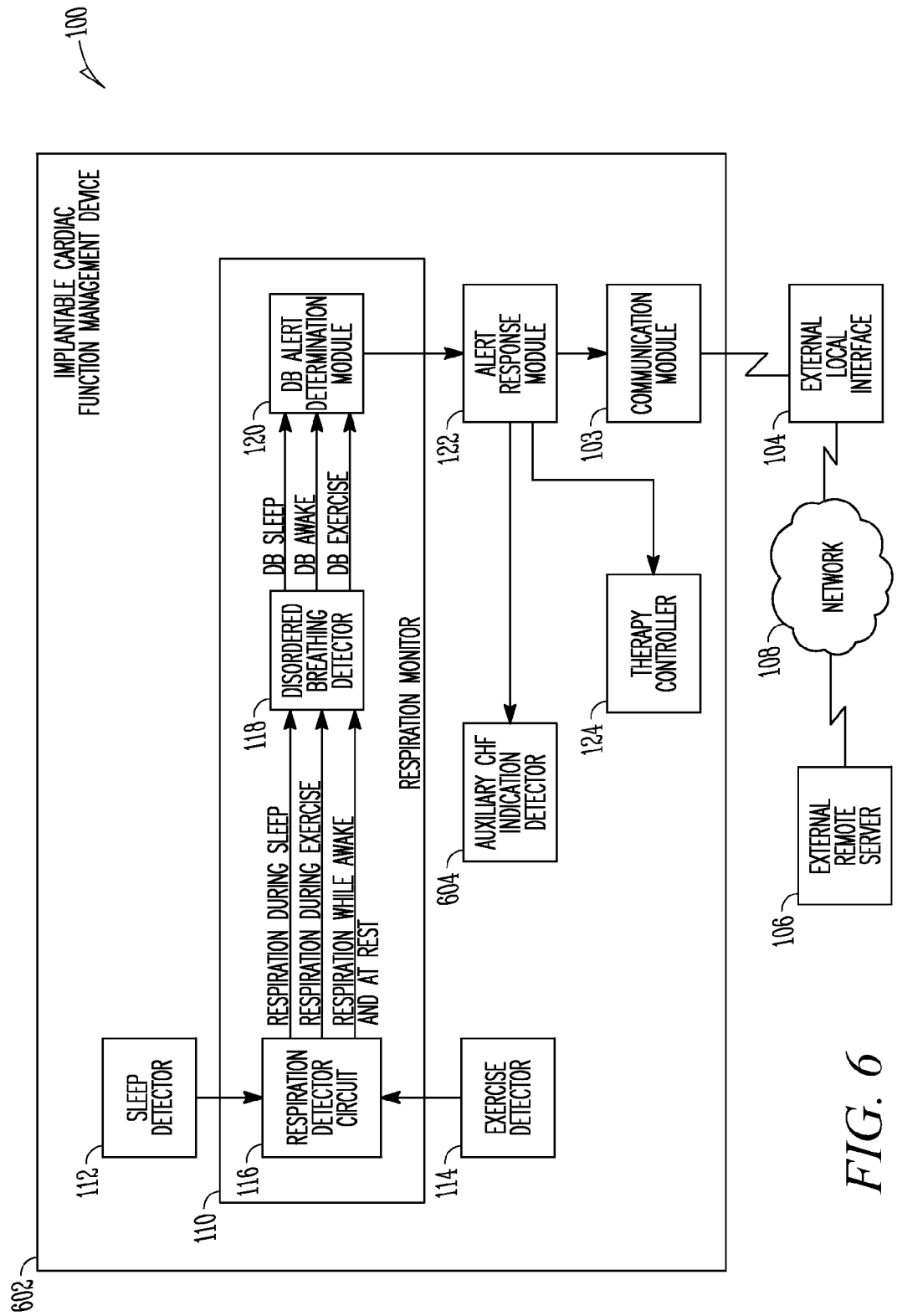
FIG. 6 is a block diagram of an example, similar to FIG. 1, in which the implantable cardiac function management device includes a detector for another CHF symptom, such as a pulmonary fluid accumulation detector.

Disordered breathing and periodic breathing can be symptomatic of congestive heart failure (CHF). Therefore, in generating any alert based on disordered breathing or periodic breathing, it may be desirable to qualify or otherwise base such alert on one or more other detected symptoms of CHF. For example, FIG. 6 illustrates a block diagram of an example, similar to FIG. 1, in which the implantable cardiac function management device 602 includes an auxiliary CHF indication detector 604. As an illustrative example, the auxiliary CHF indication detector 604 includes a pulmonary fluid accumulation detector to detect accumulation of pulmonary fluid, which is another symptom of CHF. The pulmonary fluid accumulation detector can measure transthoracic impedance, which will tend to decrease as pulmonary fluid accumulates in the thorax. The pulmonary fluid accumulation detector can itself include a posture detector, to reduce or eliminate the effect of postural changes in thoracic impedance measurements to get a more accurate representation of pulmonary fluid accumulation. Other examples of the auxiliary CHF indication detector 604 include a pulmonary artery pressure sensor, a heart sound sensor, a heart rate variability (HRV) sensor, a patient weight indicator (which may receive information communicated from an external weight scale), a patient activity sensor, or the like. The auxiliary CHF indication detector 604 can also combine multiple such sensors to provide various indications of CHF.

In the example in which the auxiliary CHF indication detector 604 includes a pulmonary fluid accumulation detector, an indication of detected pulmonary fluid can be provided to the alert response module 122. The indication of detected pulmonary fluid can be used to generate a separate alert, or to qualify an alert based on disordered or periodic breathing, such that both pulmonary fluid accumulation and one or both of disordered or periodic breathing is required in order to trigger the responsive alert. Alternatively or additionally, the pulmonary fluid accumulation indication (or any other appropriately weighted indications of one or more other CHF symptoms) can be appropriately weighted and combined with the disordered breathing indication (or any other appropriately weighted indications of one or more other CHF symptoms) to create a CHF status indicator representative of a CHF patient's wellness or sickness based on multiple symptoms.

Figure 7:
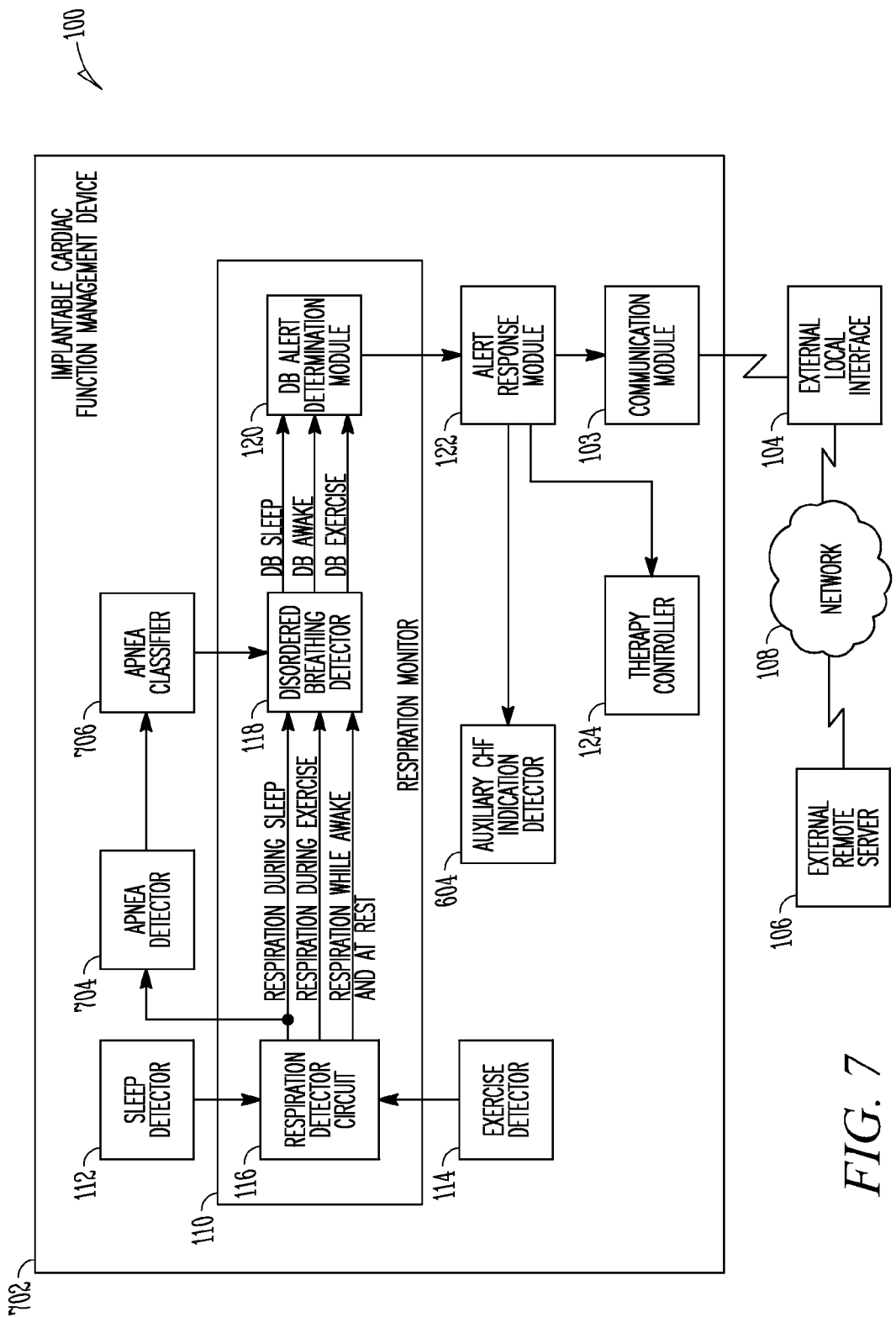
FIG. 7 is a block diagram of another example of an implantable cardiac function management device that includes an apnea detector and an apnea classifier.

FIG. 7 is a block diagram of another example of an implantable cardiac function management device 702 that includes an apnea detector 704 and an apnea classifier 706. In this example, the apnea detector 704 receives respiration during sleep information from the respiration detector 116, and detects incidences of apnea. The apnea detector 704 provides information about detected incidences of apnea to the apnea classifier 706, which classifies the apnea, for example, as obstructive sleep apnea (OSA) or central sleep apnea (CSA). One illustrative example of a sleep apnea detector and classifier is described in Patangay et al. U.S. patent application Ser. No. 11/425,820, filed on Jun. 22, 2006, entitled APNEA TYPE DETERMINING APPARATUS AND METHOD, which is incorporated herein by reference in its entirety, including its description of an apnea detector and classifier.

Since CSA is more likely to be indicative of CHF than OSA, the apnea classification information provided by the apnea classifier 706 to the disordered breathing detector 118 can be used to either: (1) qualify the disordered breathing during sleep density or severity indicator, such that only CSA episodes are counted, and CSA episodes are not counted; or (2) provide separate disordered breathing during sleep density or severity indicators to separately count incidences of OSA and CSA, with the DB alert determination module 120 formulating its alert based on these separate indicators similar to the manner described above.

Although the above description has emphasized an example in which processing is generally carried out within an implantable device, it should be understood that information derived from the respiration signal obtained from the implantable device can be communicated to external local interface 104 or external remote server 106 to perform such processing at such other locations. Moreover, such processing can include information from one or more devices that are not implanted. For example, a body weight measurement as measured by an external weight scale could be combined with a disordered breathing indication obtained from an implantable cardiac function management device, e.g., during processing at external remote server 106, to generate a CHF wellness indicator or to trigger an alert or responsive therapy.

In certain examples, information from the disordered breathing detector 118 (e.g., indications of disordered breathing density or severity in sleep, exercise, or awake but resting states) can be provide to the communication module 103, and communicated to the external local interface 104 or the external remote server 106, such as for storage or for display on a monitor, for example, as separate trends of disordered or periodic breathing density or severity in sleep, exercise, or awake but resting states, or as histograms of disordered or periodic breathing density or severity in sleep, exercise, or awake but resting states, or in any other useful form.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A method comprising:
    detecting a sleep indication in a subject, the sleep indication providing an indication or inference of whether the subject is asleep or awake;
    detecting an exercise indication in the subject, the exercise indication providing an indication or inference of whether the subject is active or at rest; and
    monitoring respiration of the subject using a respiration monitor, including:
        detecting disordered breathing in the subject;
        receiving the sleep indication and the exercise indication; and
        computing a sleep disordered breathing indication (DBsleep) indicative of disordered breathing occurring when the sleep indication indicates or infers that the subject is asleep, an exercise disordered breathing indication (DBexercise) indicative of disordered breathing occurring when the exercise indication indicates or infers that the subject is active, and a resting awake disordered breathing indication (DBrest) indicative of disordered breathing occurring when the sleep indication indicates or infers that the subject is awake and the exercise indication indicates or infers that the subject is at rest, wherein the monitoring respiration includes computing a combined disordered breathing metric, DBtotal, according to DBtotal=A·DBsleep+B·DBexercise+C·DBrest, wherein A, B, and C are independently specifiable scaling values.

2. The method of claim 1, comprising generating an alert in response to an abnormal value of at least one of: the sleep disordered breathing indication, the exercise disordered breathing indication, and the resting awake disordered breathing indication.

3. The method of claim 2, comprising automatically delivering a therapy in response to the alert.

4. The method of claim 1, comprising:
    monitoring an auxiliary indication of congestive heart failure of the subject; and
    generating an alert in response to an abnormal value of the auxiliary indication of congestive heart failure and an abnormal value of at least one of: the sleep disordered breathing indication, the exercise disordered breathing indication, and the resting awake disordered breathing indication.

5. The method of claim 4, wherein monitoring the auxiliary indication of congestive heart failure includes monitoring at least one of a pulmonary fluid accumulation, a pulmonary artery pressure, a heart sound, a heart rate variability, a patient weight, and a patient activity level.

6. The method of claim 4, comprising automatically delivering a therapy in response to the alert.

7. The method of claim 1, comprising displaying information about at least one of a sleep disordered breathing indication, an exercise disordered breathing indication, and a resting awake disordered breathing indication.

8. The method of claim 1, comprising:
    detecting one or more apnea events;
    classifying the one or more apnea events as obstructive sleep apnea (OSA) or central sleep apnea (CSA); and
    determining the sleep disordered breathing indication using information about the classification of the one or more apnea events as OSA or CSA.

9. The method of claim 8, comprising determining a first sleep disordered breathing indication using only CSA events.

10. The method of claim 9, comprising determining a second sleep disordered breathing indication using only OSA events.

11. A method comprising:
    detecting a sleep indication in a subject, the sleep indication providing an indication or inference of whether the subject is asleep or awake;
    detecting an exercise indication in the subject, the exercise indication providing an indication or inference of whether the subject is active or at rest;
    detecting disordered breathing in the subject using a respiration monitor, including:
        receiving the sleep indication and the exercise indication; and
        computing at least two of: a sleep disordered breathing indication indicative of disordered breathing occurring when the sleep indication indicates or infers that the subject is asleep, an exercise disordered breathing indication indicative of disordered breathing occurring when the exercise indication indicates or infers that the subject is active, and a resting awake disordered breathing indication indicative of disordered breathing occurring when the sleep indication indicates or infers that the subject is awake and the exercise indication indicates or infers that the subject is at rest; and
    generating an alert in response to at least an abnormal value or a specified increase in at least two of: the sleep disordered breathing indication, the exercise disordered breathing indication, and the resting awake disordered breathing indication.

12. The method of claim 11, comprising automatically initiating or adjusting therapy in response to the alert.

13. The method of claim 11, comprising:
    detecting or measuring an auxiliary congestive heart failure (CHF) indication; and
    generating the alert in response to the auxiliary CHF indication and an abnormal value or a specified increase of at least two of: the sleep disordered breathing indication, the exercise disordered breathing indication, and the resting awake disordered breathing indication.

14. The method of claim 13, wherein detecting or measuring the auxiliary CHF indication includes detecting or measuring a pulmonary fluid accumulation, wherein the auxiliary CHF indication includes an indication of an abnormally high level of pulmonary fluid.

15. The method of claim 13, wherein detecting or measuring the auxiliary CHF indication includes detecting or measuring at least one of a pulmonary artery pressure, a heart sound, a heart rate variability, a patient weight, and a patient activity.

16. The method of claim 13, comprising automatically initiating or adjusting therapy in response to the alert.

17. The method of claim 11, wherein detecting disordered breathing includes:
   detecting a respiration signal from the subject;
   detecting an envelope of the respiration signal; and
   detecting a variation in the envelope representing disordered breathing.

18. The method of claim 11, comprising displaying information about at least one of a sleep disordered breathing indication, an exercise disordered breathing indication, and a resting awake disordered breathing indication.

19. The method of claim 18, wherein displaying the information includes displaying a trend over time of at least one of a sleep disordered breathing indication, an exercise disordered breathing indication, and a resting awake disordered breathing indication.

20. The method of claim 11, comprising distinguishing between obstructive sleep apnea (OSA) and central sleep apnea (CSA) using an apnea classifier; wherein the sleep disordered breathing indication uses information from the apnea classifier to determine the sleep disordered breathing indication.

* * * * *